United States Patent [19]

Hon et al.

[11] E Re. 28,990

[45] Reissued Oct. 5, 1976

[54] BIPOLAR ELECTRODE STRUCTURE FOR MONITORING FETAL HEARTBEAT AND THE LIKE

[75] Inventors: Edward H. Hon; Robert W. Hon, both of Bradbury, Calif.

[73] Assignee: Corometrics Medical Systems, Inc., Wallingford, Conn.

[22] Filed: Feb. 6, 1975

[21] Appl. No.: 547,716

Related U.S. Patent Documents

Reissue of:

[64] Patent No.: 3,827,428
Issued: Aug. 6, 1974
Appl. No.: 311,764
Filed: Dec. 4, 1972

U.S. Applications:

[63] Continuation-in-part of Ser. No. 108,034, Jan. 20, 1971, abandoned.

[52] U.S. Cl. ..... 128/2.06 E; 128/418; 128/DIG. 4

[51] Int. Cl.[2] ..... A61B 5/04

[58] Field of Search ..... 128/2.06 E, 2.06 R, 128/2.1 E, 2.1 R, 404, 418, DIG. 4

[56] References Cited

UNITED STATES PATENTS

| | | | |
|---|---|---|---|
| 2,102,270 | 12/1937 | Hyams | 128/303.17 |
| 2,839,049 | 6/1958 | MacLean | 128/2 B |
| 2,890,266 | 6/1959 | Bollmeier | 174/87 |
| 3,087,486 | 4/1963 | Kilpatrick | 128/2.1 E |
| 3,120,227 | 2/1964 | Hunter, Jr. et al. | 128/2.06 E |
| 3,216,424 | 11/1965 | Chardack | 128/418 |
| 3,222,755 | 12/1965 | Grass | 128/2.06 E |
| 3,253,595 | 5/1966 | Murphy, Jr. et al. | 128/418 |
| 3,326,207 | 6/1967 | Egan | 128/2.06 E |
| 3,348,548 | 10/1967 | Chardack | 128/418 |
| 3,410,269 | 11/1968 | Hovick | 128/329 |
| 3,416,534 | 12/1968 | Quinn | 128/418 |
| 3,420,223 | 1/1969 | Day et al. | 128/2.06 E |
| 3,472,234 | 10/1969 | Tachick | 128/418 |
| 3,474,791 | 10/1969 | Benton | 128/418 |
| 3,494,364 | 2/1970 | Peters | 128/303.17 |
| 3,533,403 | 10/1970 | Woodson | 128/2.06 E |
| 3,580,242 | 5/1971 | La Croix | 128/2.06 E |
| 3,737,579 | 6/1973 | Bolduc | 128/418 |
| 3,750,650 | 8/1973 | Ruttgers | 128/2.06 E |
| 3,800,784 | 4/1974 | Kiszel et al. | 128/2.06 E |
| 3,835,864 | 9/1974 | Rasor | 128/418 |
| 3,844,292 | 10/1974 | Bolduc | 128/418 |

FOREIGN PATENTS OR APPLICATIONS

| | | | |
|---|---|---|---|
| 2,004,422 | 8/1971 | Germany | 128/2.06 E |

OTHER PUBLICATIONS

Kuahama et al., "Japanese Journal of Medical Electronics & Biomedical Journal," vol. 5, No. 3, 7/67, pp. 199–201.

Ruttgers et al., article – no citation given, pp. 654–660.

La Croix, "Michigan Medicine", Aug. 1968, pp. 976–979.

Caldeyro-Barcia et al., – Digest – 1961, International Conference on Medical Electronics, p. 1.

Smyth, The Lancet, June 6, 1933, pp. 1124–1126.

Japanese Article – No translation or citation given.

Junge, "Geburtshilfe und Frauenheilkeit," vol. 29, pp. 129–133, 1969.

Hon, "Obstetrics & Gynecology", vol. 30, No. 2, Aug. 1967, pp. 281–286.

Hon, "American Journal of Obstetrics & Gynecology", vol. 86, No. 6, July 15, 1963, pp. 772–784.

Hon, "The Yale Journal of Biology & Medicine", vol. 39, No. 1, Aug. 1966, pp. 54–58.

Hon et al., "American Journal of Obstetrics & Gynecology", vol. 79, No. 5, May 1960, pp. 1012–1023.

Hunter, Jr. et al., "Obstetrics & Gynecology", vol. 16, No. 5, Nov. 1960, pp. 567–570.

Hon, "The Yale Journal of Biology & Medicine", vol. 32, No. 5, April 1960, pp. 397–399.

Hon, "Connecticut Medicine", vol. XXIV, No. 5, May 1960, pp. 289–293.

Hon et al., "Obstetrics & Gynecology", vol. 40, No. 3, Sept. 1972, pp. 362–365.

*Primary Examiner*—William E. Kamm
*Attorney, Agent, or Firm*—Darby & Darby

[57] ABSTRACT

An improved electrode system for monitoring fetal heartbeat includes a curved guide tube adapted to be inserted through the vagina and cervix of a woman in labor, a retaining coil mounted on a holder member which is slidably disposed in the guide tube, a flexible driving tube adapted to rotate the holder member to screw the retaining coil into a fetal epidermis and two spaced electrodes which are adapted to be electrically connected to a suitable apparatus for monitoring fetal heartbeat. In the first disclosed embodiment of the invention one of the electrodes is a pointed member mounted in the holder which mounts the retaining coil. The retaining coil, when screwed into the fetal epidermis, maintains the pointed first electrode in piercing engagement with the fetus. In the second disclosed embodiment the retaining coil and the first electrode are one and the same structure, i.e., the first electrode is in the form of a coil which is adapted to screw into the fetal epidermis. In both of the embodiments disclosed the second electrode is spaced from the first electrode and electrical contact between the two electrodes is established by vaginal and cervical secretions of the woman in labor. Driving connection between the holder member and the flexible driving tube is provided by slots in the forward end of the driving tube and fin means on the holder. In the second embodiment disclosed the second electrode is in the form of a flat member mounted on the rear end of the holder and serves as the fin means.

36 Claims, 10 Drawing Figures

BIPOLAR ELECTRODE STRUCTURE FOR MONITORING FETAL HEARTBEAT AND THE LIKE

Matter enclosed in heavy brackets [ ] appears in the original patent but forms no part of this reissue specification; matter printed in italics indicates the additions made by reissue.

This applicaton is a continuaton-in-part of U.S. Pat. application Ser. No. 108,034, filed Jan. 20, 1971, *now abandoned*.

The present invention relates to an improved bipolar electrode structure adapted to be inserted through the vagina and cervix of a woman in labor, into contact with the fetus. The electrode structure is designed to be operatively connected to an amplifier and a cardiotachometer for recording the fetal electrocardiogram and heart rate during labor and delivery.

It has long been recognized that monitoring fetal heartbeat is a most important procedure during the conduct of labor. Various types of methods and apparatuses for performing this monitoring function have been designed in recent years. The most successful and practical techniques are those employing electrodes which are attached to the fetus.

One such technique is described in Volume 35, No. 1, of Obstetrics and Gynecology, January 1970 issue, pages 111–113. The technique there described utilizes a vaginal endoscope and specially designed forceps to apply a silver electrode to the fetal scalp.

A second type of electrode structure for recording fetal heartbeat is described in Volume 16, No. 5 of Obstetrics and Gynecology, November 1960 edition, pages 567–570, The electrode structure there described is a unipolar structure comprising a spring steel clip adapted to be closed by a sliding plastic sleeve to engage the fetal scalp or buttocks.

The foregoing electrode structures give rise to several problems which the structure of the present invention is designed to overcome. Both the "forceps-endoscope" and the "sliding sleeve-clip" types of electrodes cannot be applied until the mother's cervix has dilated to about 2.0 cm, and thus cannot ordinarily be applied during the very early stages of labor.

Another disadvantage associated with the foregoing types of electrodes is that both include clips which must be squeezed onto the fetal epidermis. These clips are extremely thin and brittle and are often cracked or damaged by mechanical stresses during application. Such cracks create electrical "noise" in the electrocardiogram system during the fetal heartbeat monitoring operation, and thus interfere with such monitoring studies.

The foregoing types of electrodes are also relatively difficult to apply and remove. The "forceps-endoscope" system reqires a specially designed lighting apparatus which must be used to insure proper application of the electrode.

In view of the foregoing, it is an object of the present invention to provide a vaginal electrode structure which overcomes the foregoing problems associated with the prior art electrode structures.

A further object of the present invention is to provide an improved, durable, vaginal electrode structure which can be quickly and effectively applied to the fetus during a relatively early stage of labor, and which can be quickly and easily removed.

DESCRIPTION OF EMBODIMENT OF FIGS. 1–7

Figure 1:
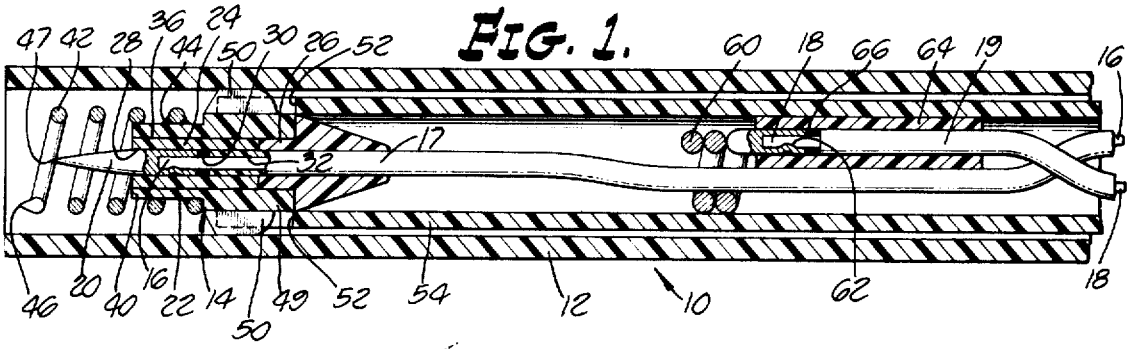
FIG. 1 is a sectional side elevational view of the forward portion of a first preferred embodiment of the electrode structure of the present invention, with the various parts thereof positioned as they would be prior to use.
Figure 2:
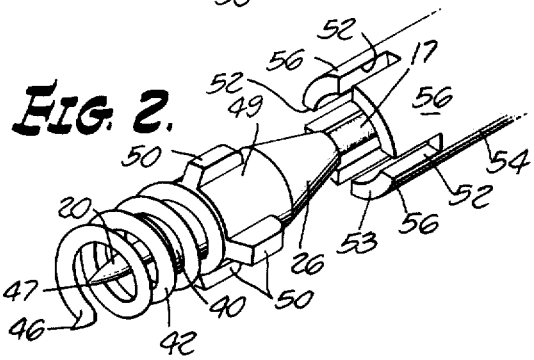
FIG. 2 is a perspective view of the holder member, first electrode, retaining coil and the forward end of the driving tube of the electrode structure shown in FIG. 1.
Figure 3:
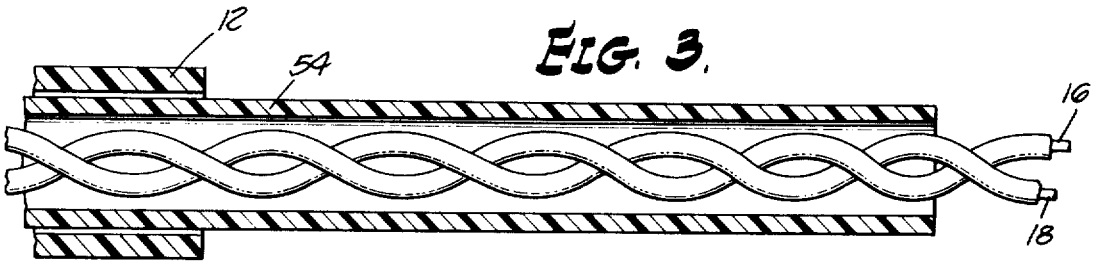
FIG. 3 is a sectional side elevational view of the rear portion of the electrode structure shown in FIGS. 1 and 2.

Referring now to the drawings, the electrode structure 10 illustrated in FIGS. 1, 2 and 3 comprises a guide tube 12 having an open forward end through which a holding member 14 is movable, and an open rear end through which electrode wires 16, 18 extend. The guide tube 12 is curved *and form-sustaining* (see FIGS. 5–7) to facilitate insertion of the tube through the vagina and cervix of a woman in labor.

One of the wires 16 extends through the holding member 14 and is electrically connected to a pointed electrode 20 which is preferably made of silver-silver chloride. The desirability of using a silver-silver chloride electrode is discussed in some detail in Volume 30, No. 2 of Obstetrics & Gynecology, August 1967 issue, pages 281–286. The electrode 20 is preferably crimped on the forward end of wire 16, as at 22 (FIG. 1) and soldered thereto to insure a good electrical connection.

An insulating sleeve 24 covers the juncture of the first wire 16 and the first electrode 20. Epoxy adhesive 26 fills and seals the annular space between the insulation 17 of wire 16 and the interior wall of the holder 14, behind the sleeve 24. The epoxy 26 also covers and seals the rear end of the holder 14.

Epoxy adhesive is also provided in the annular space 28 between the electrode 20 and the interior wall of tube 24, in the annular space 30 between the wire 16 and the interior wall of the tube 24, in the annular space between the wire insulation 17 and the interior wall of tube 24, and in the annular space 36 between the exterior wall of tube 24 and the interior wall of the holder 14. The epoxy adhesive at these locations insures a good seal from the forward end of the holder 14.

The forward end 40 of the holder 14 has a retaining coil 42 mounted thereon by means of a suitable adhesive 44 (e.g., epoxy). The retaining coil 42 (which may be plastic, metal or any other suitable material) is provided with a pointed forward end 46 to pierce the fetal epidermis. When the holding member 14 and the retaining coil 42 are rotated the retaining coil will "screw" into the fetus and bring the first electrode 20 into engagement with the fetal epidermis with the pointed tip 47 piercing the epidermis. The forward end 40 of the holder 14 acts as a "stopper" which limits the distance which the tip 47 of the first electrode 20 can travel into the fetus. The distance between the pointed end 46 of the retaining coil 42 and the forward end 40 of the holder member 14 is relatively small (e.g., about 1/16 of an inch).

As best shown in FIG. 2, the rear portion 49 of the holder member 14 is provided with a plurality of radially outwardly extending, circumferentialy spaced wings of fins 50,50,50,50, which are adapted to be releasably engaged by circumferentially spaced slots 52,52,52,52, in the forward end 53 of a flexible driving tube 54. *The guide tube 12 is more rigid than the flexible driving tube 54 so that the guide tube will maintain its curved configuration when the flexible driving tube is rotated within it.*

The flexible driving tube 54 (preferably made of plastic) extends through the curved guide tube 12 for rotating the holder 14 and the retaining coil 42. As noted above, rotation of the holder 14 by the flexible driving tube 54 is accomplished via the slots 52 in the forward end 53 of the driving tube and the fins 50 on the holder. It should be noted that the driving connection between the fins 50 and the slots 52 is relatively "loose" so that the driving tube 54 will "slip" around the holder fins 50 when the holder meets with a relatively slight amount of resistance to rotation. Thus, when the holder 14 meets with resistance to rotation (e.g., when the first electrode 20 has pierced the fetal epidermis and the forward end of the holder has come into contact with the fetus), continued rotation of the driving tube 54 will not drive the retaining coil or first electrode further into the fetus. This "loose driving connection" may be accomplished by making the fins 54 or the driving tube segments 56 between the slots 52 "soft" or pliable enough so that they will bend and "slip" relative to one another when the holder 14 resists rotation.

Referring to FIG. 1, it will be seen that the forward end of the second conductor 18 terminates within the guide tube 12 substantially behind the holder 14. A silver-silver chloride electrode coil 60 is crimped (as at 62, FIG. 1) and soldered onto the forward end of the second conductor 18. The coil [20] *60* is the second electrode in the system and also functions to hold the conductors 16, 18 adjacent to one another.

A plastic insulating sleeve 64 is provided around the juncture of the electrode coil 60 and the second conductor 18 to eliminate or minimize any electrical noise which otherwise might be created if the juncture of the conductor 18 and the electrode coil 60 were exposed to vaginal fluids when the system is in use.

Epoxy adhesive is preferably provided between the interior wall of the insulating sleeve 64 and the rear end of the coil electrode 60 to seal the forward end of the insulating sleeve. Epoxy adhesive is also preferably provided between the conductor 18 and the interior wall of the insulating sleeve 64 (as at 66, FIG. 1), and between the interior wall of the insulating sleeve 64 and the insulation cover 19 on the second conductor 18 to seal these junctures.

Figure 4:
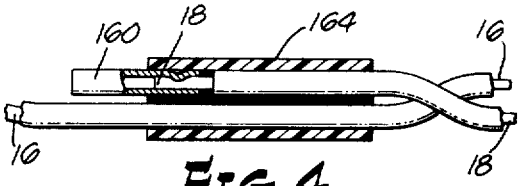
FIG. 4 is a sectional side elevational view showing the electrode structure of FIGS. 1–3 with a modified form of the second electrode.

In FIG. 4, an alternative structure for the second electrode is shown. In the FIG. 4 embodiment the second electrode 160 is in the form of a sleeve which is crimped and soldered onto the forward end of the second conductor 18 and an insulating sleeve 164 encloses both of the conductors 16, 18. Epoxy adhesive is preferably provided in the FIG. 4 structure to seal the juncture between the electrode sleeve 160 and the conductor 18 from vaginal fluids.

As best shown in FIG. 1, the electrode structure 10 of the present invention is packaged so that the retaining coil 42 and the first electrode 20 are well behind the forward end of the guide tube 12, thereby protecting the retaining coil and electrode from damage prior to use.

Figure 5:
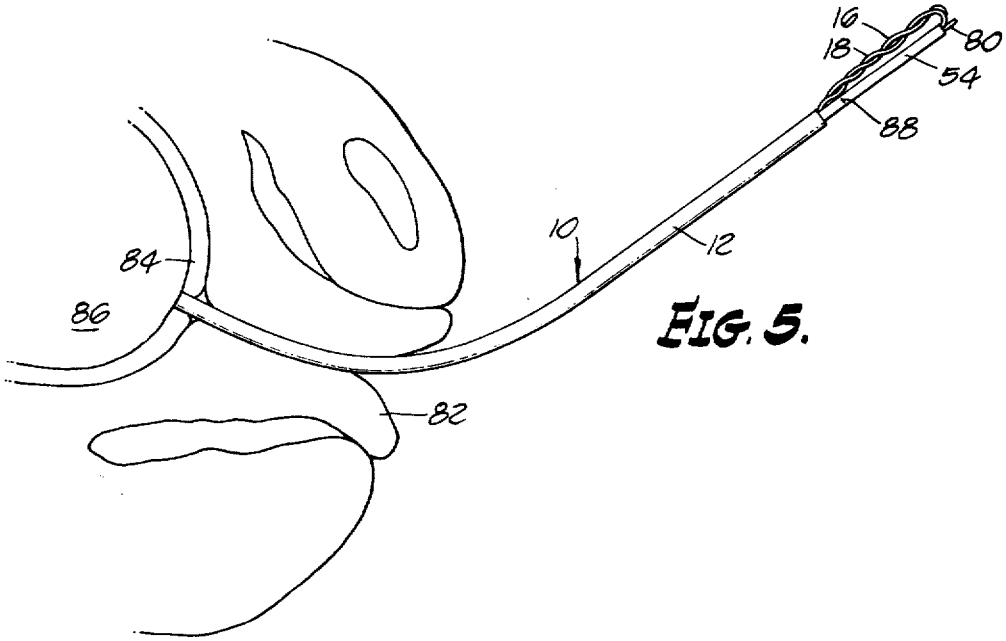
FIGS. 5, 6 and 7 are diagrammatic views illustrating the manner in which the improved electrode structure of the present invention is applied to a fetus.

As best shown in FIG. 5, the rear ends of the wires 16, 18 are folded back and inserted between the rear end of the curved guide tube 12 and the rear portion of the flexible driving tube 54. A wedge 80 (FIGS. 5 and 7) may be inserted in the rear end of the driving tube 54 to [prevent relative sliding movement between the flexible driving tube and the wires 16, 18.] *wedge the wires 16 and 18 against the interior surface of the driving tube 54. Since wire 16 is secured to the holder 14, if the wires are pulled, the fins 50 are urged toward slots 52 of the driving tube. Accordingly, if the wires 16 and 18 are held with the fins 50 engaging slots 52 of the driving tube, the wires then aid in locking the holder and driving tube together during insertion of the electrode.*

Figure 6:
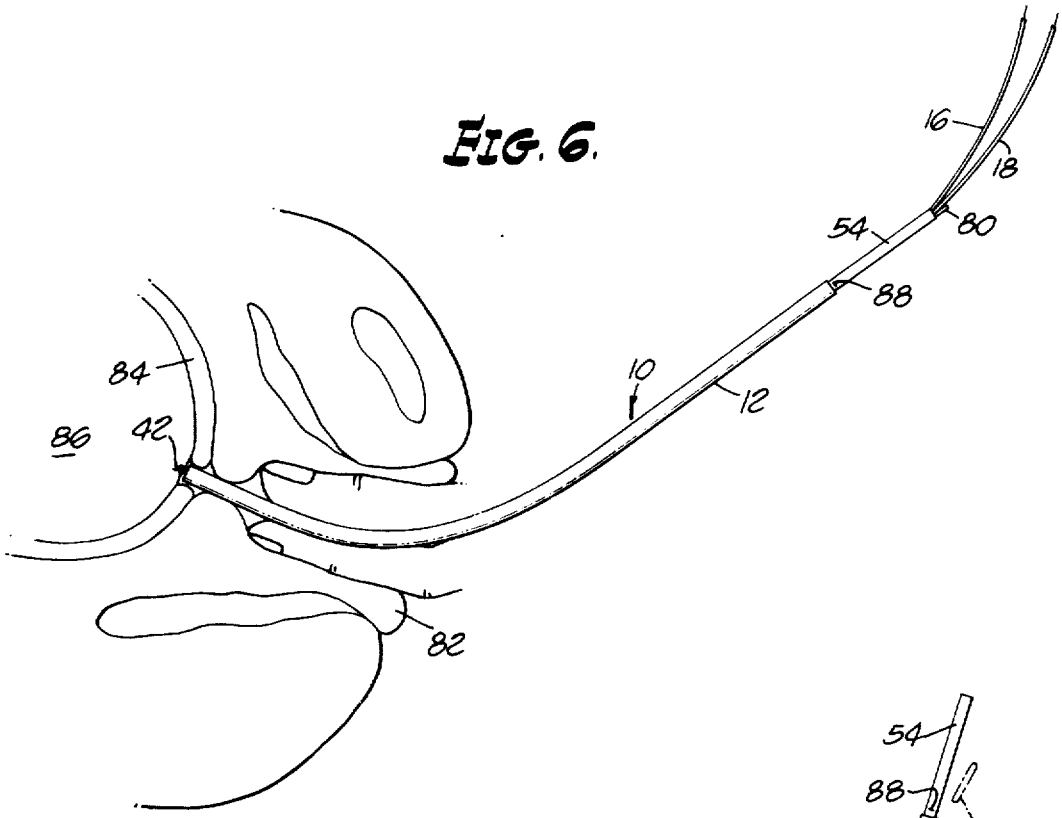
Figure 7:
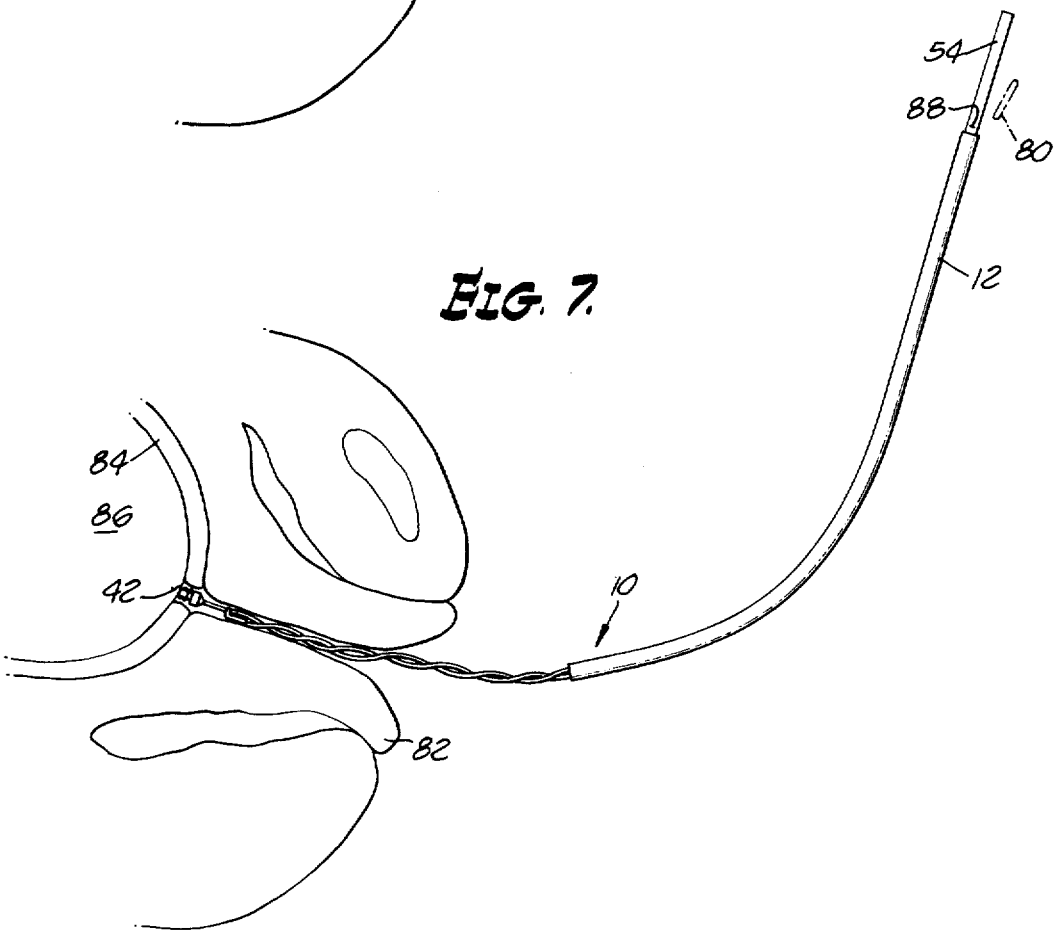

The method of using the electrode structure 10 of the present invention is illustrated diagrammatically in FIGS. 5, 6 and 7.

With the first and second electrodes, 20 and 60, disposed within the guide tube 12, the doctor inserts the forward end of the curved guide tube through the mother's vagina 82 and cervix 84 until the forward end of the guide tube makes contact with the fetal head 86 (or other portion of the fetus), as shown in FIG. 5. The doctor then removes the folded-back ends of the wires 16, 18 from between the rear ends of the guide tube 12 and the driving tube 54 to permit relative sliding movement between these tubes. While holding the forward end of the guide tube 12 stationary, the doctor then pushes the rear end of the flexible driving tube 54 forwardly until the retaining coil 42 makes contact with the fetal epidermis (FIG. 6). An indicator mark 88 (FIGS. 5–7) may be provided on the driving tube 54 to visually warn the doctor when the retaining coil 42 has passed beyond the forward end of the guide tube 12.

When the doctor feels or sees that the retaining coil 42 has contacted the fetal epidermis 86, he rotates the flexible driving tube 54 (e.g., about one full turn) while maintaining the forward end of the guide tube 12 against the fetal head. This will screw the retaining coil 42 into the fetal epidermis and drive the pointed end of the first electrode 20 into the epidermis (see FIG. 6). It will be appreciated that the flexible construction of the driving tube 54 permits it to slide and rotate in the curved guide tube 12.

The wedge 80 is then removed from the rear end of the driving tube 54 to [permit relative sliding movement between the wires 16, 18 and] *release wires 16 and 18 with respect to driving tube 54 and thereby permit disengagement of the interlocking fins 50 and slots 52 by withdrawal of* the driving tube. The doctor then removes his fingers from the mother's vagina 82, grasps the outer ends of the driving tube and the guide tube, and slides these tubes (as a unit) off of the wires 16, 18 leaving only the electrodes 20 and 60, and the very thin wires 16, 18 within the mother.

The outer ends of the wires 16, 18 are then connected to suitable apparatus (not shown) for monitoring fetal heartbeat.

DESCRIPTION OF THE EMBODIMENT OF FIGS. 8–10

Figure 8:
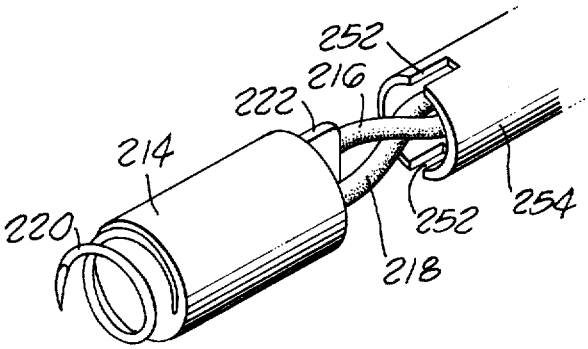
FIG. 8 is a perspective view of a second preferred embodiment of an electrode structure constructed according to the teachings of the present invention, wherein the retaining coil serves as the first electrode and wherein the first and second electrodes are mounted on the same holder.
Figure 9:
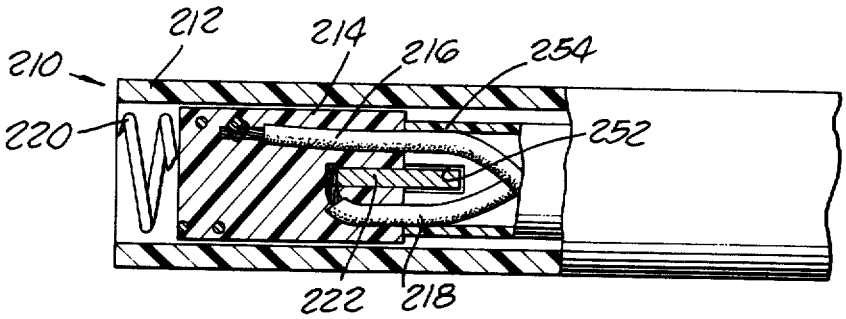
FIG. 9 is a sectional side elevational view of the electrode structure shown in FIG. 8 with the various parts thereof positioned as they would be prior to use.
Figure 10:
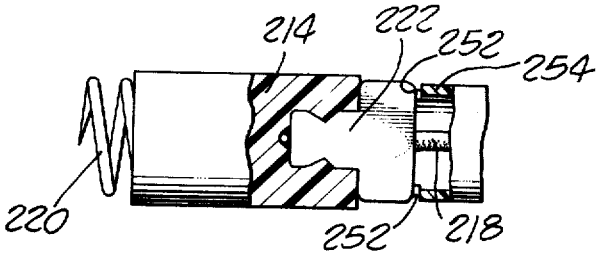
FIG. 10 is a side elevational view, partly in section, showing the electrode unit rotated 90 degrees from the position illustrated in FIG. 9.

FIGS. 8–10 illustrate a second preferred embodiment of the electrode structure of the present invention wherein the first electrode serves as the retaining coil and the second electrode is mounted on the holder member and serves as the fin means which cooperates with the slots in the forward end of the flexible driving tube to provide the driving connection between the holder and the driving tube.

Referring to FIG. 9, the electrode structure 210 comprises a curved, *form-sustaining* guide tube 212 having an open forward end through which a holder member 214 is adapted to pass. The holder member 214 has a spiral electrode 220 mounted in its forward end and a generally flat electrode 222 mounted in its rear end.

*As shown in FIG. 9, the diameter of the cylindrical holder member 214 approximates the inner diameter of guide tube 212. Consequently, the holder member prevents lateral movement of the electrode coil 220 (relative to the guide tube) while the coil is being attached to the fetus. Moreover, the length of the holder member 214 is such that when the spiral electrode 220 extends just beyond the end of the guide tube 212 (for attachment to the fetus), the cylindrical holder member within the guide tube prevents skewing of the coil. These features help to reduce the possibility of injury to the fetus when the electrode is being applied.*

A first electrode wire 216 extends through the rear end of the holder member 214 and is electrically connected to the rear end of spiral electrode 220. A second electrode wire 218 also extends through the rear end of holder member 214 and is electrically connected to the forward end of the second electrode 222.

Both electrodes, 220 and 222, are preferably constructed of stainless steel and are soldered to their respective electrode wires, 216 and 218. The holder member 214 is made of an insulative material, such as plastic, and electrically isolates the electrodes 220 and 222 from one another.

A flexible driving tube 254 is slidably and rotatably disposed in the curved guide tube 212 for rotating the holder 214 to screw the spiral electrode 220 into a fetal epidermis. As best shown in FIG. 8, the forward end of the driving tube 254 is provided with a pair of slots 252, 252 which are adapted to receive the rearwardly extending portion of the plate electrode 222. When the slots 252, 252 on the forward end of the holder 214 engage the plate electrode 222 the holder 214 and the spiral electrode 220 may be rotated by rotating the flexible driving tube 254.

The electrode wires, 216 and 218, extend rearwardly through the rear portion (not shown) of the driving tube 254 and the rear portion (not shown) of the guide tube 212 for connection to a suitable apparatus (not shown) for monitoring fetal heartbeat.

The electrode structure 210 is used in the same manner as described above and illustrated in FIGS. 5–7 in connection with the structure of FIGS. 1–7. In use, with the spiral electrode 220, holder 214 and plate electrode 222 disposed within the curved guide tube 212, behind the forward end thereof, the doctor inserts the forward end of the guide tube 212 through the woman's vagina and cervix until the forward end of the guide tube makes contact with the fetal head (or other portion of the fetus) in the same manner as described above in connection with the electrode structure 10 illustrated in FIGS. 1–7. The doctor then holds the forward end of the guide tube 212 stationary and pushes the rear end of the flexible driving tube 254 forwardly until the spiral electrode 220 makes contact with the fetal epidermis.

When the doctor feels or sees that the spiral electrode 220 has contacted the fetal epidermis, he rotates the flexible driving tube 254 while maintaining the guide tube 212 against the fetal head to screw the spiral electrode 220 into the fetal epidermis.

It is intended that the present invention be limited only by the scope of the appended claims.

We claim:

1. An apparatus for use in monitoring fetal heartbeat and the like comprising:

a [relatively rigid] *form-sustaining*, curved guide tube adapted to be inserted through the vagina and cervix of a woman in labor;

a holder member slidably and rotatably disposed in said guide tube;

a retaining coil mounted on said holder member and adapted to be screwed into a fetal epidermis by rotating the holder member;

monitoring means mounted on said holder member;

a flexible drive tube slidably and rotatably disposed in said curved guide tube for moving said holder member through said guide tube to bring said retaining coil into engagement with a fetal epidermis and for rotating said holder member to screw said retaining coil into the epidermis; [and]

*said guide tube being more rigid than said drive tube so that said guide tube will maintain its curved configuration when said flexible drive tube is rotated within it; and* cooperating means on said drive tube and said holder member for rotating said holder member and said retaining coil by rotating said drive tube.

2. The apparatus according to claim 1, wherein said retaining coil comprises a first electrode.

3. The apparatus according to claim 2, and further comprising a second electrode mounted on said holder member and spaced from said first electrode; said holder member comprising insulating material.

4. The apparatus according to claim 1, and further comprising a first electrode mounted on said holder member and adapted to contact the epidermis into which the said retaining coil is screwed.

5. The apparatus according to claim 1, wherein said drive tube has a substantially uniform outer diameter throughout the length thereof, and said guide tube has a substantially uniform inside diameter throughout the length thereof; the outer diameter of said drive tube being smaller than the inside diameter of said guide tube, whereby said drive tube may be freely slid forwardly and rearwardly in said guide tube.

6. An improved electrode structure for monitoring fetal heartbeat and the like comprising:

an elongated, [relatively flexible] *form-sustaining*, [rigid], relatively narrow guide tube having an open forward end adapted to be inserted through the vagina and cervix of a woman in labor;

a generally cylindrical holder member slidably and rotatably disposed within said guide tube; said holder member having a forward end portion and a rear end portion;

a plurality of circumferentially-spaced driving fins on the rear end portion of said holder member;

a retaining coil mounted on the forward end portion of said holder member; said retaining coil terminating in a pointed forward end spaced forwardly of the forward end of said holder member;

a first electrode mounted in said holder member; said first electrode including a rear portion mounted in said holder member, and a pointed forward end extending through the forward end of said holder member; said pointed forward end of said first electrode terminating rearwardly of the pointed forward end of said retaining coil;

a first electrical wire conductor having a forward end extending through the rear end of said holder member and electrically connected to said first electrode;

insulating means covering the juncture of said first electrode and said first electrical wire conductor;

an elongated, relatively flexible driving tube slidably and rotatably disposed in said guide tube; said driving tube having a forward end provided with a plurality of axially-extending, circumferentially-spaced driving slots releasably engaging said driving fins on said holder member for rotating said holder member when said driving tube is rotated;

*said guide tube being more rigid than said driving tube so that said guide tube will maintain its curved configuration when said flexible driving tube is rotated within it;* a second electrode slidably disposed within said driving tube, rearwardly of said slotted forward end thereof;

a second electrical wire conductor having a forward end electrically connected to said second electrode;

insulation means covering the juncture of said second electrical wire conductor and said second electrode;

said first and second electrical wire conductors having rear ends extending out of the rear ends of said driving tube and said guide tube for connection to an electrical monitoring apparatus.

7. An improved electrode structure according to claim 6, wherein said driving tube is longer than said guide tube, and has a rear end portion extending rearwardly of the [reare] *rear* end of said guide and further comprising an indicator mark on said rear end portion of said driving tube for indicating to the user when the pointed forward end of said retaining coil approaches the forward end of said guide tube.

8. An improved electrode structure according to claim 6, wherein said second electrode is formed in the shape of a coil [, ] encircling said first electrical wire to hold said first and second electrical wires adjacent one another.

9. An improved electrode structure according to claim 6, wherein said first electrode is made of a silver-silver chloride composition.

10. An improved electrode structure according to claim 6, wherein said second electrode is formed in the shape of a tubular sleeve.

11. An improved electrode structure for use in monitoring fetal heartbeat and the like comprising:

a [relatively rigid] *form-sustaining*, curved elongated guide tube having an open forward end adapted to be inserted through the vagina and cervix of a woman in labor;

holder means slidably and rotatably disposed in said guide tube;

a retaining coil connected to said holder means and adapted to engage a fetal epidermis;

a flexible driving tube slidably and rotatably disposed in said guide tube for driving said retaining means into engagement with a fetal epidermis; said [drive] *driving* tube having a forward end; and means on said forward end of said driving tube operatively connected to said retaining coil for rotating said retaining coil to screw said coil into the fetal epidermis;

*said guide tube being more rigid than said driving tube so that said guide tube will maintain its curved configuration when said flexible driving tube is rotated within it;* an electrode mounted on said holder means; and means for electrically connecting said electrode to an electrical monitoring apparatus.

12. An improved electrode structure according to claim 11, wherein said electrode comprises a pointed electrode spaced from said retaining coil, and wherein said retaining coil is adapted to maintain said pointed electrode in engagement with the fetal epidermis when said retaining coil is screwed into the fetal epidermis.

13. An improved electrode structure according to claim 11, wherein said electrode includes at least a portion of said retaining coil.

14. An improved electrode structure according to claim 11, wherein said electrode comprises a silver-silver chloride electrode.

15. An improved electrode structure according to claim 11, wherein said retaining coil is mounted on one end of said holder member; fin means on the other end of said holder member; and wherein said means on said forward end of said driving tube comprises a plurality of slots releasably engaging said fin means on said holder member for rotating said holder member and said retaining coil when said driving tube is rotated.

16. An improved electrode structure according to claim 11, and further comprising a second electrode disposed in said guide tube rearwardly of said first electrode, and means for electrically connecting said second electrode to an electrical monitoring apparatus.

17. An improved structure for use in monitoring fetal heartbeat and the like comprising;

a [relatively rigid] *form-sustaining*, elongated, curved guide tube having an open forward end adapted to be inserted through the vagina and cervix of a woman in labor;

a holder member slidably and rotatably disposed within said guide tube; said holder member having a forward end portion and a rear end portion;

a retaining coil mounted on the forward end portion of said holder member; said retaining coil terminating in a pointed forward end spaced forwardly of the forward end of said holder member;

electrode means mounted on said holder member;

an elongated, relatively flexible driving tube slidably and rotatably disposed in said guide tube; [and]

*said guide tube being more rigid than said driving tube so that said guide tube will maintain its curved con-*

*figuration when said flexible driving tube is rotated within it; and* cooperating engaging means on said rear end portion of said holder member and the forward end portion of said driving tube for rotating said holder member and said retaining coil by rotating said driving tube.

18. An apparatus for monitoring fetal heartbeat and the like comprising:

a [relatively rigid] *form-sustaining* guide tube having an open forward end; said guide tube being curved to conform to and fit the angular anatomical configuration of a woman's vagina and cervix so as to be adapted to be comfortably inserted through the vagina and cervix of a woman in labor;

a holder member adapted to be slidably and rotatably disposed in said guide tube; said holder member having a forward end and a rear end;

an electrode coil mounted on said forward end of said holder member and being adapted to be screwed into an epidermis when said holder member is rotated; said electrode coil having a pointed forward end adapted to pierce an epidermis;

a flexible driving tube adapted to be slidably and rotatably disposed in said curved guide tube for selectively moving and rotating said holder member and said electrode coil; said driving tube having a forward end;

*said guide tube being more rigid than said driving tube so that said guide tube will maintain its curved configuration when said flexible driving tube is rotated within it;* cooperating drive means on said driving tube and on said holder member for rotating said holder member and said electrode coil when said driving tube is rotated; and means for electrically connecting said electrode coil to an electrical monitoring apparatus.

19. The apparatus according to claim 18 and further comprising a second electrode mounted on said rear end of said holder member and spaced from said first electrode; said holder member comprising insulating material electrically insulating said first and second electrodes from one another.

20. The apparatus according to claim 19, wherein said second electrode comprises a generally flat member, and wherein said cooperating drive means comprises slots in the forward end of said driving tube and a portion of said flat second electrode.

21. An improved structure for use in monitoring fetal heartbeat and the like comprising:

a [relatively rigid] *form-sustaining*, elongated guide tube having an open forward *end*; said guide tube being curved to conform to and fit the angular anatomical configuration of a woman's vagina and cervix so as to be adapted to be confortably inserted through the vagina and cervix of a woman in labor;

a holder member slidably and rotatably disposed within said guide tube; said holder member having a forward end portion and a rear end portion;

a retaining coil mounted on the forward end portion of said holder member; said retaining coil terminating in a pointed forward end spaced forwardly of the forward end of said holder member;

monitoring means mounted on said holder member;

an elongated, relatively flexible driving tube slidably and rotatably disposed in said guide tube; [and]

*said guide tube being more rigid than said driving tube so that said guide tube will maintain its curved configuration when said flexible driving tube is rotated within it; and* cooperating engaging means on said rear end portion of said holder member and the forward end portion of said driving tube for rotating said holder member and said retaining coil by rotating said driving tube; said cooperating engaging means on said rear end portion of said holder member and on the forward end portion of said driving tube establishing a relatively loose connection so that the engaging means on the forward end of said driving tube will slip around said engaging means on the rear end portion of said holder member when the holder member meets with a predetermined amount of resistance to rotation.

22. An improved structure according to claim 21, wherein said cooperating engaging means on said rear end of said holder member and the forward end of said driving tube comprise fin means on one of said holder member or said driving tube and slots in the other of said holder member or said driving tube.

23. An improved structure for use in monitoring fetal heartbeat and the like comprising:

a [relatively rigid] *form-sustaining*, elongated guide tube having an open forward *end*, said guide tube being curved to conform to and fit the angular anatomical configuration of a woman's vagina and cervix so as to be adapted to be comfortably inserted through the vagina and the cervix of a woman in labor;

a holder member slidably and rotatably disposed within said guide tube; said holder member having a forward end portion and a rear end portion;

a retaining coil mounted on the forward end portion of said holder member; said retaining coil terminating in a pointed forward end spaced forwardly of the forward end of said holder member;

monitoring means mounted on said holder member;

an elongated, relatively flexible driving tube slidably and rotatably disposed in said guide tube; [and]

*said guide tube being more rigid than said driving tube so that said guide tube will maintain its curved configuration when said flexible driving tube is rotated within it; and* fin means on said rear end of said holder member and means defining slots in the forward end of said driving tube for releasably engaging said fin means and rotating said holder member and said retaining coil by rotating said driving tube; the portions of the forward end of said driving tube between said slots being relatively soft and flexible to establish a relatively loose connection with said fin means so that the forward end of said driving tube will slip around said fin means on the rear end portion of said holder member when the holder member meets with a predetermined amount of resistance to rotation.

24. An apparatus for use in monitoring fetal heartbeat and the like comprising:

a holder member;

a retaining coil mounted on said holder member and adapted to be screwed into a fetal epidermis by rotating the holder member;

monitoring means mounted on said holder member;

an elongated tube for moving said holder member to bring said retaining coil into engagement with a fetal epidermis and for rotating said holder member to screw said retaining coil into the epidermis; and slots in the forward end of said tube and fin means on said holder member, whereby said holder member and said retaining coil may be rotated by rotating said tube.

25. An improved electrode structure for use in monitoring fetal heartbeat and the like comprising:

holder means having fin means thereon;

a retaining coil connected to said holder means and adapted to engage a fetal epidermis;

a driving tube for driving said retaining means into engagement with a fetal epidermis; said drive tube having a forward end; and slots in said forward end of said driving tube operatively connected to said fin means on said holder means for rotating said holder means and said retaining coil to screw said coil into a fetal epidermis;

an electrode mounted on said holder means; and means for electrically connecting said electrode to an electrical monitoring apparatus.

26. An improved structure for use in monitoring fetal heartbeat and the like comprising:

a [relatively rigid] *form-sustaining*, elongated outer tube having an open forward end adapted to be inserted through the vagina and cervix of a woman in labor;

a holder member slidably and rotatably disposed within said outer tube; said holder member having a forward end portion and a rear end portion;

a retaining coil mounted on the forward end portion of said holder member; said retaining coil terminating in a pointed forward end spaced forwardly of the forward end of said holder member;

monitoring means mounted on said holder member;

an elongated driving tube disposed in said outer tube; [ and ]

*said guide tube being more rigid than said driving tube so that said guide tube will maintain its curved configuration when said flexible driving tube is rotated within it; and* fin means on said holder member and slots in the forward end portion of said driving tube for rotating said holder member and said retaining coil by rotating said driving tube.

*27. A fetal electrode structure for use in monitoring fetal heartbeat, comprising:*

*an elongated, cylindrical, form-sustaining guide tube curved to conform to and fit the angular anatomical configuration of a woman's vagina and cervix so as to be comfortably inserted through the vagina and cervix of a woman in labor, said guide tube having a forward end and a rear end and being adapted to maintain its curved configuration when a flexible driving tube is rotated within it;*

*a cylindrical holder slidably and rotatably disposed in said guide tube, said holder being made of an electrically insulating material and having a forward end surface and a rear end surface, the length and diameter of the holder being such as to prevent substantial lateral movement and skewing of said holder relative to said guide tube when the forward portion of said holder extends from said guide tube;*

*an electrode coil extending from the front end surface of said cylindrical holder and terminating in a forward, pointed end adapted to pierce a fetal epidermal layer;*

*a second electrode extending rearwardly from the rear end surface of said cylindrical holder, said second electrode being electrically insulated from said electrode coil;*

*a flexible driving tube slidably and rotatably disposed in said guide tube, said driving tube having a forward end and a rear end, said guide tube being more rigid than said driving tube;*

*first and second wires passing through said driving tube into the rear end surface of said holder and electrically contacting said electrode coil and second electrode, respectively, said wires extending from the rear end of said driving tube;*

*cooperating engaging means on the rear end surface of said holder and the forward end of said driving tube for releasably connecting said driving tube and said holder for rotating said holder about its axis within said guide tube.*

*28. A fetal electrode structure according to claim 27, further comprising means for selectively holding said wires at the rear end of said driving tube for locking said cooperating engaging means together.*

*29. A fetal electrode structure according to claim 27, wherein said cooperating engaging means comprises said second electrode and slots in the forward end of said driving tube for engaging said second electrode.*

*30. A fetal electrode structure according to claim 29, wherein said second electrode comprises a flat plate.*

*31. A fetal electrode structure according to claim 27, wherein said second electrode comprises a flat metal plate.*

*32. A fetal electrode structure according to claim 30, further comprising means for selectively holding said wires at the rear end of said driving tube for locking said cooperating engaging means together.*

*33. A fetal electrode structure according to claim 27, including means on said driving tube for indicating when said electrode coil extends a preselected distance beyond the forward end of said guide tube.*

*34. A fetal electrode structure according to claim 27, wherein the outer diameter of said driving tube is less than the diameter of said holder.*

*35. A fetal electrode structure for use in monitoring fetal heartbeat, comprising:*

*a form-sustaining, elongated cylindrical guide tube curved to conform to and fit the angular anatomical configuration of a woman's vagina and cervix so as to be comfortably inserted through the vagina and cervix of a woman in labor, having a forward end and a rear end;*

*a cylindrical holder having a front face and a rear face, the cylindrical surface of said holder engaging the inner surface of said guide tube for enabling slidable movement and rotation of said holder within said guide tube;*

*an electrode coil extending from the front face of said cylindrical holder and terminating in a forward, pointed end adapted to pierce a fetal epidermal layer;*

*a flat electrode fin perpendicular to the rear face of said cylindrical holder, said electrode fin substantially located on a diameter of said rear face and being electrically insulated from said electrode coil;*

*a relatively flexible driving tube slidably and rotatably disposed in said guide tube, said driving tube having a forward end and a rear end;*

*said guide tube being more rigid than said driving tube so that said guide tube will maintain its curved con-*

*figuration when said flexible driving tube is rotated within it;*

*first and second wires passing through said driving tube into the rear face of said holder and electrically contacting said electrode coil and flat electrode fin, respectively, said wires extending rearwardly from the rear end of said driving tube;*

*slots in the forward end of said driving tube for releasably engaging said electrode fin; and*

*means for selectively holding said wires at the rear end of said driving tube for locking said slots and flat electrode fin together.*

*36. A fetal electrode structure according to claim 35, wherein said driving tube includes arcuate drive segments between said slots, said arcuate drive segments being sufficiently pliable to slip over said electrode fin when the rotational drive force transmitted from said driving tube to said holder exceeds a predetermined limit.*

* * * * *

UNITED STATES PATENT OFFICE

CERTIFICATE OF CORRECTION

Patent No. RE. 28,990 Dated October 5, 1976

Inventor(s) EDWARD H. HON; ROBERT W. HON

It is certified that error appears in the above-identified patent and that said Letters Patent are hereby corrected as shown below:

Column 3, line 20, "of" should be -- or --.

Column 6, last line "[rigid]," should be deleted.

Column 7, line 53, after "guide" the word -- tube -- should appear.

Signed and Sealed this

Seventh Day of February 1978

[SEAL]

*Attest:*

RUTH C. MASON
*Attesting Officer*

LUTRELLE F. PARKER
*Acting Commissioner of Patents and Trademarks*